(12) United States Patent
Jin et al.

(10) Patent No.: US 9,345,647 B2
(45) Date of Patent: May 24, 2016

(54) EPOXY-CONTAINING DENTAL COMPOSITION CURABLE BY MULTIPLE POLYMERIZATION MECHANISMS

(75) Inventors: Shuhua Jin, Irvine, CA (US); Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 543 days.

(21) Appl. No.: 13/377,441

(22) PCT Filed: Jun. 11, 2010

(86) PCT No.: PCT/US2010/038293
§ 371 (c)(1),
(2), (4) Date: Feb. 27, 2012

(87) PCT Pub. No.: WO2010/144787
PCT Pub. Date: Dec. 16, 2010

(65) Prior Publication Data
US 2012/0142807 A1    Jun. 7, 2012

Related U.S. Application Data

(60) Provisional application No. 61/186,063, filed on Jun. 11, 2009.

(51) Int. Cl.
| | | |
|---|---|---|
| *A61K 6/08* | (2006.01) | |
| *A61K 6/00* | (2006.01) | |
| *C08G 59/17* | (2006.01) | |
| *C08G 59/42* | (2006.01) | |
| *C08L 63/00* | (2006.01) | |
| *C08F 222/10* | (2006.01) | |

(52) U.S. Cl.
CPC .............. *A61K 6/0038* (2013.01); *A61K 6/0017* (2013.01); *A61K 6/0023* (2013.01); *C08G 59/1466* (2013.01); *C08G 59/42* (2013.01); *C08L 63/00* (2013.01); *C08F 222/1006* (2013.01)

(58) Field of Classification Search
CPC .......................... A61K 6/0038; A61K 6/0017
USPC ............ 522/65, 182, 171, 180; 525/119, 121, 525/107, 113–116; 433/224, 226, 228.1; 523/118
See application file for complete search history.

(56) References Cited

U.S. PATENT DOCUMENTS

| | | |
|---|---|---|
| 3,066,112 A | 11/1962 | Bowen |
| 3,179,623 A | 4/1965 | Bowen |
| 3,194,784 A | 7/1965 | Bowen |
| 3,450,613 A | 6/1969 | Steinberg |
| 3,751,399 A | 8/1973 | Lee, Jr. |
| 3,926,906 A | 12/1975 | Lee, II et al. |
| 4,544,359 A | 10/1985 | Waknine |
| 4,547,531 A | 10/1985 | Waknine |
| 5,276,068 A | 1/1994 | Waknine |
| 5,444,104 A | 8/1995 | Waknine |
| 5,624,976 A | 4/1997 | Klee |
| 6,013,694 A | 1/2000 | Jia et al. |
| 6,270,562 B1 | 8/2001 | Jia |
| 6,306,926 B1 | 10/2001 | Bretscher et al. |
| 6,403,676 B1 | 6/2002 | Jia et al. |
| 6,417,246 B1 | 7/2002 | Jia et al. |
| 6,653,365 B2 | 11/2003 | Jia |
| 6,787,629 B2 | 9/2004 | Jia et al. |
| 7,275,932 B2 | 10/2007 | Jin et al. |
| 7,367,524 B2 | 5/2008 | Burnett |
| 2007/0088097 A1* | 4/2007 | Qian ............................. 523/115 |
| 2007/0197682 A1* | 8/2007 | Jia et al. ....................... 523/116 |
| 2008/0160206 A1* | 7/2008 | Burtscher et al. ............. 427/450 |
| 2008/0299513 A1 | 12/2008 | Jia |
| 2009/0048364 A1 | 2/2009 | Liu |
| 2009/0233252 A1* | 9/2009 | Cinader, Jr. ....................... 433/9 |

FOREIGN PATENT DOCUMENTS

| | | |
|---|---|---|
| DE | 19937093 A1 | 2/2001 |
| EP | 295784 A2 | 12/1988 |
| EP | 1133971 A1 | 9/2001 |
| WO | 9718792 A1 | 5/1997 |
| WO | 9915570 A1 | 4/1999 |
| WO | 9962460 A1 | 12/1999 |

OTHER PUBLICATIONS

Dentsply DeTrey, AH Plus Root Canal Sealer, Scientific Compendium, Apr. 19, 2005, 26 pp.; downloaded from: http://www.dentsply.de/bausteine.net/file/showfile.aspx?downdaid=7299&sp=D&domid=1042&fd=2.
3M ESPE, Filtek LS, LS System Adhesive, Technical Product Profile, 40 pp.; downloaded from: http://multimedia.3m.com/mws/mediawebserver?mwsId=SSSSSu7zK1fslxtUNY_9M8_Sev7qe17zHvTSevTSeSSSSSS-.
European Search Report, PCT/US2010/038293, filed Jun. 6, 2011, mailed Sep. 1, 2010, 11 pp.

* cited by examiner

*Primary Examiner* — Michael Pepitone
(74) *Attorney, Agent, or Firm* — Wood, Herron & Evans, LLP

(57) ABSTRACT

Polymerizable compositions are provided that contain an epoxy compound and a polymerizable, ethylenically-unsaturated resin having an acid functional group where the epoxy compound is polymerized by cationic polymerization initiated by the acid functional group and the polymerizable, ethylenically-unsaturated resin is polymerized by free-radical polymerization. To that end, a two-part polymerizable composition is provided that has a first part containing the epoxy compound; and a second part containing the polymerizable, ethylenically-unsaturated resin having an acid functional group. The first part and/or the second part further contain a radical initiator effective to initiate either self-curing or light-curing by free-radical polymerization.

20 Claims, No Drawings

EPOXY-CONTAINING DENTAL COMPOSITION CURABLE BY MULTIPLE POLYMERIZATION MECHANISMS

CROSS-REFERENCE TO RELATED APPLICATIONS

Pursuant to 37 C.F.R. §1.78, this application claims the benefit of and priority to prior filed co-pending PCT Patent Application PCT/US10/038293, which was filed on Jun. 11, 2010 and claims priority to Provisional Patent Application Ser. No. 61/186,063, filed Jun. 11, 2009, which are expressly incorporated herein by reference in their entirety.

FIELD OF INVENTION

The present invention relates to adhesive and/or sealant compositions that cure by cationic polymerization and free-radical polymerization, and particularly to self-adhering dental compositions suitable for use as a root canal sealer.

BACKGROUND OF INVENTION

Methacrylate resin-based compositions have been used in dentistry for decades. However, dental materials based on (meth)acrylate resins, which are chemically cured, usually have wet surfaces due to the inhibition of the free-radical polymerization reaction at the surface by molecular oxygen. The oxygen inhibition is even more apparent as the rate of polymerization of the material decreases. This presents a potential problem with the restoration of a tooth. For example, when the oxygen inhibition effect takes place in an interface, such as at the tooth surface of a root canal, unsatisfactory sealing may result.

Alternatively, compositions cured by epoxy ring-opening polymerization have been used to seal root canals. For example, products, such as AH 26® Silver Free and AH PLUS JET® by Dentsply, are commercially-available, two-part epoxy-amine compositions. While compositions cured by epoxy ring-opening polymerization are not susceptible to the oxygen inhibition effect, as described above, two drawbacks to these conventional epoxy and amine two-component systems are slower reaction times at room temperature, and lack of adhesion to a tooth surface. Additionally, the slow curing time inhibits the material from possessing instant mechanical properties because the setting time of the material can take hours, if not days.

Compositions cured by epoxy ring-opening polymerization may also be initiated through a cationic polymerization of the epoxy resin using a starter, such as a Lewis acid or a strong Brønsted acid. For example, Lewis acids, such as $BF_3.Et_2O$, $BF_3.THF$, $AlCl_3$, $FeCl_3$ and the like, where $Et_2O$ is diethyl ether and THF is tetrahydrofuran, may initiate the cationic ring-opening polymerization under ambient conditions. Similarly, strong Brønsted acids, such as $HBF_4$, $HB(C_6F_5)_4$, $HPF_6$, $HAsF_6$ or $HSbF_6$ may initiate the cationic ring-opening polymerization immediately after mixing with the epoxy.

Another type of initiator for the cationic ring-opening polymerization is a latent starter, which upon contact with the epoxy does not itself initiate the polymerization, but starts the polymerization upon contact with an agent that transforms the starter into a form that is able to initiate the polymerization. For example, halonium salts of the general formula $Hal\text{-}(Ar)_2^+An^-$, wherein Hal is a halogen, Ar is an aryl group, and An is an anion, when transformed can liberate $H^+$ as extremely strong acid $H^+An^-$. An exemplary latent starter is diaryliodonium compounds, such as diphenyliodonium tetrafluoroborate, diphenyliodonium hexafluorophosphate and the like. Generally, Cu(I) salts and a reducing agent, such as ascorbic acid, are used to transform the halonium salt.

Additionally, the use of light-initiated cationic ring-opening polymerization of epoxy resins in dentistry has grown in recent years, largely due to the lower shrinkage of the resulting composite as compared to the free radical polymerization of (meth)acrylates. But these epoxy compositions cured by the methods described above can still present poor adhesion to a tooth surface.

Therefore, what is needed is a composition that possesses favorable curing properties and improved adhesion.

SUMMARY OF THE INVENTION

In one embodiment of the invention, a polymerizable composition is provided comprising a first part comprising an epoxy compound; and a second part comprising a polymerizable, ethylenically-unsaturated resin having an acid functional group, wherein the first part and/or the second part further comprises a radical initiator.

In another embodiment of the invention, a method of providing a polymerized composition is provided which comprises mixing a first part comprising an epoxy compound with a second part comprising a polymerizable, ethylenically-unsaturated resin having an acid functional group, wherein the mixing initiates a cationic polymerization reaction of the epoxy compound facilitated by the acid functional group; and polymerizing the polymerizable, ethylenically-unsaturated resin, wherein the polymerizing is a free-radical polymerization initiated by a self-cure free-radical initiator and/or an photo-initiated free radical initiator.

In another embodiment of the invention, a method of curing a two-part composition, which has a first part comprising an epoxy compound, and a second part comprising a polymerizable, ethylenically-unsaturated resin having an acid functional group, wherein the first and/or second part further comprises a self-cure free-radical initiator and/or a photo-initiated free-radical initiator, is provided wherein the method comprises effecting a first polymerization of the epoxy compound initiated by the acid functional group selected from the group consisting of a carboxylic acid, a carboxylic acid anhydride, an acyl halide, a sulfonic acid, a sulfonic anhydride, a sulfonyl halide, a sulfinic acid, a sulfinic anhydride, a sulfinyl halide, a phosphoric acid, a phosphoric acid derivative, a phosphonic acid, and a phosphonic acid derivative; and effecting a second polymerization of the polymerizable, ethylenically-unsaturated resin initiated by the self-cure free radical initiator and/or the photo-initiated free radical initiator.

In another embodiment of the invention, a kit is provided comprising a first part comprising an epoxy compound; a second part comprising a polymerizable, ethylenically-unsaturated resin having an acid functional group, wherein the first and/or second part further comprises a radical initiator, wherein the first part and the second part are provided in packaging that physically separates the first part from the second part; and instructions for mixing to effect a self-cure.

In yet another embodiment of the invention, there is provided a method of providing a polymerizable composition comprising providing a first part comprising an epoxy compound; and providing a second part comprising a polymerizable, ethylenically-unsaturated resin having an acid functional group, wherein the first and/or second part further comprises a self-cure free-radical initiator and/or a photo-initiator free-radical initiator, whereby upon mixing the first part and the second part the acid functional group is adapted to initiate a cationic polymerization of the epoxy compound; and the self-cure free-radical initiator and/or a photo-initiator free-radical initiator is adapted to initiate a free-radical polymerization of the polymerizable, ethylenically-unsaturated resin.

DETAILED DESCRIPTION OF THE INVENTION

The present invention is related to a two-part polymerizable composition having improved adhesion or bond strength to a substrate. In one exemplary embodiment, a two-part paste/paste acidic self-adhering dental composition is provided, wherein the first part comprises an epoxy compound and the second part comprises a polymerizable, ethylenically-unsaturated resin having an acid functional group and the first part and/or the second part further comprises a radical initiator.

According to one embodiment of the invention, a self-adhesive two-part paste/paste dental composition is prepared for use by mixing together an epoxy compound and a polymerizable, ethylenically-unsaturated resin having an acid functional group, along with a radical initiator. This combination provides for two modes of cure for the resinous combination: epoxy ring-opening polymerization catalyzed by the acidic functional group and free-radical polymerization of the ethylene moieties.

As used herein, the term "self-cure" means the inventive compositions can go through a chemical polymerization process when the first part and the second part are mixed together, without an external energy such as heat, light, or other radiation energies. For example, the epoxy-ring opening polymerization through the cationic reaction of the epoxy and acid group contained in the polymerizable monomer and/or through a redox reaction of a peroxide-tertiary amine initiated free radical curing for the (meth)acrylate monomer(s) in the compositions. The sequence of the various polymerization mechanisms can be simultaneous, sequential, or even delayed with respect to the other(s).

The first part of the two-part polymerizable composition may comprise epoxy resins of many different structures. These epoxy resins include monomeric epoxy compounds and epoxides of the polymeric type and may be aliphatic, cycloaliphatic, aromatic or heterocyclic. These epoxy resins generally have, on the average, about one polymerizable epoxy group per molecule, but may include about two polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexane carboxylates, typified by 3,4-epoxycyclohexylmethyl-3,4-epoxycyclohexane carboxylate, 3,4-epoxy-2-methylcyclohexylmethyl-3,4-epoxy-2-methylcyclohexane carboxylate, and bis(3,4-epoxy-6-methylcyclohexylmethyl)adipate.

Other epoxy-containing materials that are useful in this invention include glycidyl ether monomers, such as glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain epoxides, such as epichlorohydrins; alkylene oxides, e.g., propylene oxide; styrene oxide; alkenyl oxides, e.g., butadiene oxide; and glycidyl esters, e.g., ethyl glycidate.

Blends of various epoxy-containing materials are also contemplated. Examples of such blends include two or more weight average molecular weight distributions of epoxy-containing compounds, such as low molecular weight (below 200), intermediate molecular weight (200 to 10,000) and high molecular weight (above 10,000). Alternatively or additionally, the epoxy resin may contain a blend of epoxy-containing materials having different chemical natures, such as aliphatic and aromatic, or different functionalities, such as polar and non-polar.

There are a host of commercially-available epoxy resins which can be used in this invention. In particular, epoxides which are readily available include octadecylene oxide, epichlorohydrin, styrene oxide, vinylcyclohexene oxide, glycidol, glycidyl methacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexane carboxylate (e.g., "ERL-4221" or "CYRACURE UVR 6110" or "UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl)ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy)cyclohexane-meta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$-$C_{10}$ glycidyl ether (e.g., "HELOXY Modifier 7" from Shell Chemical Co.), alkyl $C_{12}$-$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), and 9,9-bis[4-(2,3-epoxypropoxy)-phenyl] fluorenone (e.g., "Epon 1079" from Shell Chemical Co.).

Additionally, the epoxy resin may be accompanied by a variety of other resins, including free radically-polymerizable resins, ionically-polymerizable resins, or combinations thereof, provided that the resins do not contain an acid functional group. Examples of free radically-polymerizable resins include, but are not limited to those resins with ethylenically unsaturated functional groups, such as (meth)acrylates; vinyl monomers, such as styrene; vinyl esters; and a variety of unsaturated cyclic monomers, such as spiro-ortho carbonates, spiro-ortho esters, vinyl cyclic ethers, and cyclic acetals.

Examples of ionically-polymerizable resins include, but are not limited to, vinyl ethers; and cyclic monomers, such as epoxies, siloranes, lactides, ϵ-caprolactones, and ϵ-caprolactams.

Examples of resins containing both free radically- and ionically-active functional groups include, but are not limited to, the resin oligomers having both an epoxy functionality and a (meth)acrylate functionality as set forth in commonly owned U.S. Pat. No. 7,241,856, which is hereby incorporated by reference.

Examples of ethylenically-unsaturated resins include those based on acrylate and methacrylate monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine, all of which are herein incorporated by reference in their entirety. Methacrylate-based monomers are particularly useful, including the condensation product of bisphenol A and glycidyl methacrylate; 2,2'-bis[4-(3-methacryloxy-2-hydroxy propoxy)-phenyl]-propane (BIS-GMA); dipentaerythritol pentaacrylate (DPEPA); pentaerythritol dimethacrylate (PEDM); the condensation product of ethoxylated bisphenol A and glycidyl methacrylate (EBPA-DMA); urethane dimethacrylate (UDMA); ethoxylated bisphenol A di(meth)acrylates including ethoxylated bisphenol A dimethacrylate (EBPDMA) as disclosed in U.S. Pat. No. 6,013,694 to Jia, et al.; the condensation product of 2 parts hydroxymethylmethacrylate and 1 part triethylene glycol bis(chloroformate) (PCDMA); polyurethane-based dimethacrylates (PUDMA) and polycarbonate modified-BisGMA (PCBisGMA) and other monomers set forth in commonly owned U.S. Pat. No. 6,787,629, which is hereby incorporated by reference.

This first part may also contain other additives, such as radiopaque and thickening fillers. Additionally, free radical initiator systems that are compatible with an epoxide functional group may also be included. For example, light initiators, such as camphorquinone (CQ); and co-initiators, such as ethyl-4-dimethyl benzoate (EDMAB); are particularly suitable for use. Self-cure initiators as reducing agents for the free-radical polymerization of methacrylates, such as bis(2-hydroxylethyl)-p-toluidine (DHEPT), dimethyl-p-toluidine (DMPT), and thioureas, may also be included. The commonly-known epoxy addition reaction polymerization initiators, such as a primary or a secondary amine should not be included.

The second part of the multi-part polymerizable composition, which comprises a polymerizable, ethylenically-unsaturated resin having an acid functional group, includes aliphatic or aromatic polymerizable resin monomers or oligomers. It is generally understood that the acid functional group facilitates the self-etching or self-adhering effect to the tooth structure, as well as acts as an initiator of the epoxy polymerization reaction. Furthermore, in one embodiment, an ionic reaction between the acid group of the ethylenically-unsaturated resin and the surface of an acid-reactive glass ionomer filler is also possible when there is water/moisture present.

These polymerizable monomers or oligomers comprise at least one acidic functional group, which includes acid-precursor functional groups, such as anhydrides. For example, an anhydride may react with water, an alcohol or the like to form a carboxylic acid. As such, an acidic functional group may be a carboxylic acid, carboxylic acid anhydride, acyl halide, sulfonic acid, sulfonyl halide, sulfonic anhydride, sulfinic acid, sulfinyl halide, sulfinic anhydride, phosphoric acid, phosphoric acid derivative, phosphonic acid, and phosphonic acid derivative, and combinations thereof. Additionally, the polymerizable monomers or oligomers comprise at least one polymerizable unsaturated carbon-carbon bond, such as an alkene functional group. In one embodiment, the polymerizable, ethylenically-unsaturated resin is an ethylenically-unsaturated carboxylic acid.

In another embodiment, the polymerizable, ethylenically-unsaturated resin contains at least two acidic functional groups. For example, the ratio between the number of acidic functional groups and the number of polymerizable unsaturated carbon-carbon bonds in the polymerizable, ethylenically-unsaturated resin may range between about 1:3 to about 3:1, for example, about 1:2 to about 2:1.

Exemplary polymerizable, ethylenically-unsaturated resins include, but are not limited to, acrylic acid, methacrylic acid, 2-(methacryloyloxy)ethyl phosphate, bis(2-(methacryloyloxy)ethyl)phosphate, biphenyl dimethacrylate, ethylene glycol methacrylate phosphate, 4-methacryloxyethyl trimellitic anhydride, 4-methacryloxyethyl trimellitic acid, adduct reaction product of pyromellitic di-anhydride with 2-hydroxyethylmethacrylate, adduct reaction product of pyromellitic di-anhydride with glycerol dimethacrylate, or adduct reaction product of benzenetetracarboxylic acid di-anhydride with 2-(6-hydroxy-1-oxo-hexyloxy)ethyl methacrylate.

Another suitable class of polymerizable, ethylenically-unsaturated resins is an ethylenically-unsaturated phosphoric acid ester having the general formula:

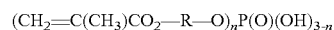

$(CH_2=C(CH_3)CO_2-R-O)_nP(O)(OH)_{3-n}$ wherein R is a substituted or un-substituted alkyl or aryl group having about 1 to about 36 carbon atoms and n equals 1 or 2.

Additionally, the second part may further include a variety of other resins that do not have an acid functional group, including free radically-polymerizable resins, ionically-polymerizable resins, or combinations thereof, as discussed above, provided that the resin is stable under reasonable storage conditions in the presence of an acid functional group and the other constituents included in this mixture. The second part may also contain other additives, such as radiopaque and thickening fillers. Self-cure initiators compatible with the acidic media may also be included. For example, oxidizing agents such as benzoyl peroxide or cumene hydroperoxide are suitable for use.

Known viscous resins may be added to the first part or the second part of the polymerizable composition. Non-limiting examples include polyurethane dimethacrylates (PUDMA), diurethane dimethacrylates (DUDMA), and/or the polycarbonate dimethacrylate (PCDMA) disclosed in U.S. Pat. Nos. 5,276,068 and 5,444,104 to Waknine, which is the condensation product of two parts of a hydroxyalkylmethacrylate and 1 part of a bis(chloroformate). Another advantageous resin having lower water sorption characteristics is an ethoxylated bisphenol A dimethacrylate (EBPDMA) as disclosed in U.S. Pat. No. 6,013,694. An especially useful methacrylate resin is the condensation product of bisphenol A and glycidyl methacrylate, 2,2'-bis[4-(3-methacryloxy-2-hydroxy propoxy)-phenyl]-propane (Bis-GMA).

Diluent monomers may be added to the first part or the second part of the polymerizable composition to increase the surface wettability of the composition and/or to decrease the viscosity of the polymerization medium. Suitable diluent monomers include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol)dimethacrylate and tetra(ethylene glycol)dimethacrylate; and diol dimethacrylates such as butanedimethacrylate, dodecanedimethacrylate, or 1,6-hexanedioldimethacrylate (HDDMA). Tri(ethylene glycol)dimethacrylate (TEGDMA) is particularly suitable for use.

Diluent monomers or viscous resins, when present, are incorporated into the polymerizable composition in an amount of about 1 to about 70 wt % of the total composition. Optionally, excess water or alcohol may be included.

As stated above, the composition further includes a radical polymerization curing system to facilitate another mechanism for curing the polymerizable resins. These initiator systems may include polymerization initiators; polymerization accelerators; ultraviolet light absorbers; antioxidants; and other additives known in the art.

A light cure system may be selected from known light-activated polymerization initiators, including but not being limited to benzil, benzoin, benzoin methyl ether, DL-camphorquinone (CQ) and benzil diketones. Either UV-activated cure or visible light-activated cure (about 230 nm to about 750 nm) is acceptable. The amount of photoinitiator may be selected according to the curing rate desired. A minimally catalytically effective amount is generally about 0.01% by weight of the polymeric components. Faster rates of cure are achieved with amounts of catalyst in the range from greater than about 0.01% to about 5% by weight of the polymeric component. Visible light curing systems may further comprise polymerization accelerators, which include various organic tertiary amines well known in the art. In visible light curable compositions, the tertiary amines may be acrylate derivatives such as dimethylaminoethyl methacrylate and, particularly, diethylaminoethyl methacrylate (DEAEMA) and aromatic tertiary amines such as ethyl dimethylamino benzoate (EDMAB) in amounts in the range from about 0.05 to about 2 weight percent, for example from about 0.1 to about 0.5 weight percent.

Alternatively, the composition may be formulated as a self-curing system. Self-curing compositions will generally contain free radical polymerization initiators, such as a peroxide in an amount of about 0.01 to about 2.0 wt % of the total resin composite material. Particularly suitable free radical initiators include lauryl peroxide, tributyl hydroperoxide, benzoyl peroxide, and cumene hydroperoxide.

Polymerization accelerators suitable for use are the various organic tertiary amines well known in the art. In visible light curable composite materials, the tertiary amines are generally acrylate derivatives, such as dimethylaminoethyl methacrylate and, particularly, diethylaminoethyl methacrylate (DEAEMA) in an amount of about 0.05 to about 0.5 wt % of the total composition.

In the self-curing compositions, the tertiary amines are generally aromatic tertiary amines. For example, tertiary aromatic amines such as ethyl 4-(dimethylamino)benzoate (EDMAB), 2-[4-(dimethylamino)phenyl]ethanol, N,N-dimethyl-p-toluidine (DMPT), and bis(hydroxyethyl)-p-toluidine are commonly useful. Such reducing agents are generally present in an amount of about 0.5 to about 4.0 wt % of the total composition. A thiourea or its derivative reducing agent may also be used in the compositions as taught by U.S. Pat. No. 7,275,932, assigned to Jin, et al.

The compositions may also comprise other additives and solvents known in the art, for example, ultra-violet light absorbers; anti-oxidants such as BHT; stabilizers; fillers; pigments; opacifiers; handling agents/rheology modifiers; fluorescence agent; antimicrobial agents; therapeutical and/or bioactive components; mineralization promoting agent or filler; and others. For example, it is useful to employ an ultraviolet absorber in an amount of about 0.05 to about 5.0 wt % of the total composition. Such UV absorbers are particularly desirable in the visible light curable compositions in order to avoid discoloration of the resin from incident ultraviolet light. Suitable UV absorbers are the various benzophenones, particularly UV-5411 available from American Cyanamid Company; and benzotriazoles known in the art, particularly 2-(2'-hydroxy-5'-methylphenyl)-benzotriazole, sold under the trademark TINUVIN® P by Ciba-Geigy Corporation, Ardsley, N.Y.

Suitable fillers may be particulate or fibrous fillers with sizes from nano-scales to micron-scales. Fillers conventionally used in the dental industry that are capable of being covalently bonded to the resin matrix itself or to a coupling agent may be included. Such fillers are described in U.S. Pat. Nos. 4,544,359 and 4,547,531, the pertinent portions of which are hereby incorporated by reference. Examples of suitable filling materials include but are not limited to amorphous silica; spherical silica; colloidal silica; barium glasses; quartz; ceramic fillers; silicate glass; hydroxyapatite; calcium carbonate; fluoroaluminosilicate; barium sulfate; quartz; barium silicate; strontium silicate; barium borosilicate; barium boroaluminosilicate; strontium borosilicate; strontium boroaluminosilicate; bioglass; dental glass ionomer filler; glass fibers; lithium silicate; ammoniated calcium phosphate; deammoniated calcium phosphate; calcium tungstate; alumina; zirconia; tin oxide; zinc oxide; calcium oxide; bismuth compounds such as bismuth oxychloride and bismuth oxide; polymer powders such as polymethyl methacrylate, polystyrene, and polyvinyl chloride; titanium dioxide; bound and nanostructured silica fillers as set forth in commonly owned U.S. Pat. No. 6,417,246, which is hereby incorporated by reference; densified and embrittled glass fibers or particles as set forth in commonly owned U.S. Pat. Nos. 6,013,694 and 6,403,676, which are hereby incorporated by reference; fibrous material and one or more forms of surface-modifying particles bonded thereto as set forth in commonly owned U.S. Pat. No. 6,270,562, which is hereby incorporated by reference; polyhedral oligomeric silsesquioxane fillers as set forth in U.S. Pat. No. 6,653,365, which is hereby incorporated by reference; nanostructures such as POSS™ (polyhedral oligomeric silsesquioxane) supplied by Hybrid Plastics; and combinations of all the fillers mentioned. Particularly suitable fillers for dental filling-type materials prepared are those having a particle size in the range from about 0.01 to about 10 µm, together with a colloidal silica or fumed silica having particle sizes in the range from about 0.001 to about 0.07 µm.

A coupling agent may be used with the filler or the filler may be pretreated with a coupling agent, such as a silane coupling agent. For example, a commonly used coupling agent in the dental industry is γ-methacryloxypropyltrimethoxy silane.

In one particular embodiment, the composition may further include an acid-reactive filler, such as a glass ionomer (GI) filler. Contact between the acid functional group and the acid-reactive GI filler, in the presence of water or moisture, facilitates a self-hardening in the dark due to an ionic reaction between the acidic group and the surface of the GI filler. This provides a complementary polymerization to the epoxy ring-opening and free-radical polymerizations, as discussed above.

Therefore, according to embodiment of the invention, a two-part composition is provided wherein the first part comprises an epoxy-containing compound, and optionally non-epoxy containing compounds which can be (meth)acrylates without acidic groups; and a second part comprises a polymerizable, ethylenically-unsaturated resin having an acid functional group. The weight ratio between epoxy-containing compound and polymerizable, ethylenically-unsaturated resin having an acid functional group can vary depending on the type of acid and epoxy, as well as the applications. In one embodiment, the range is from about 1:10 to about 10:1; for example about 1:5 to about 5:1. A suitable radical polymerization initiator may be included in one or both of the aforementioned parts.

As such, a convenient procedure can be realized when the two-part polymerizable composition is pre-packaged, such that the desired mixing ratio is provided upon use. For example, a dental composition may be packaged in a dual-syringe assembly, two individual non-joined syringes, two tubes, two capsules, one capsule where the two pastes are segregated and do not come in contact with each other, blister packs, etc., as known to one skilled in the art. The above are examples of pre-packaged containers, which provide the first part and the second part in packaging that physically separates the first part from the second part.

The dual-syringe assembly may be fitted with a static mixer/tip so that the two pastes are mixed in the static mixer to result in a homogenous or a substantially homogenous composition which flows out from the tip. The dental practitioner can dispense the homogeneously mixed composition directly to a dental substrate, resulting in significant time savings and convenience in addition to improved adhesion.

This invention is illustrated by the following examples that are merely for the purpose of illustration and are not to be regarded as limiting the scope of the invention or the manner in which it can be practiced.

EXAMPLES

Materials used for the following examples are set forth in Table A below. The recited percentage for a specific additive included in a given resin component is a weight percentage based on the total weight of the resin component.

TABLE A

Materials used in examples.

| Abbreviation | Chemical Name | Producer |
|---|---|---|
| UVR6110 | Cyracure ™ Cycloaliphatic epoxide resin | Dow Chemical |
| Epoxy 06 | Cycloaliphatic epoxide resin equivalent to UVR6110 | Synasia, NJ |
| BADGE | Bisphenol A diglycidyl ether - DER332 | Dow Chemical |
| BFDGE | Bisphenol F diglycidyl ether | Sigma Aldrich |
| RDGE | Resorcinol digycidylether | Sigma Aldrich |
| NGDGE | Neopentyl glycol diglycidyl ether | Sigma Aldrich |
| 4-MET | 4-Methacryloxyethyl trimellitic acid | Pentron |
| HEMA | 2-Hydroxyethyl methacrylate | Degussa |
| MMA | Methacylic acid | Sigma Aldrich |
| BEPMA | Bis[2-(Methacryloyloxy)-ethyl] phosphate | Sigma Aldrich |
| EGPMA | Ethylene glycol methacrylate phosphate | Sigma Aldrich |
| TEGDMA | Triethyleneglycol dimethacrylate | Esstech, PA |
| R7200 | Silane treated fumed silica based on Aerosil A200 | Degussa Corp |
| GI | Glass ionomer filler, 4 micron particles | IndustrialCorporation |
| BiOCl | Bismuth oxychloride | Engelhard |
| CaWO$_4$ | Calcium Tungstate | Sigma Aldrich |
| Barite | Barium Sulfate | Sachtleben Corp. |

Example 1

Cationic Curing Test of Epoxy with Various Acidic Methacylates

For the curing tests of Example 1, the compositions utilized for the epoxy pastes (UVR6110, BFDGE/TEGDMA, BADGE/TEGDMA, RDGE and NGDGE) and the acidic methacrylate pastes (4-MET/HEMA, MMA, BEPMA and EGPMA) are shown in Table 1. The BADGE/TEGDMA resin was prepared by mixing BADGE and TEGDMA in 90/10 weigh ratio. The 4-MET/HEMA resin was prepared by mixing 4-MET with HEMA in 67/33 weight ratio. The remaining resins (MMA, EGPMA and UVR6110) were used as received. The resin and fillers were mixed together and yielded a flowable consistency. The curing tests were performed at 38° C. by mixing an equivalent portion, by weight, of each epoxy paste and each acidic methacrylate paste. By monitoring the gel times of the curing samples, the chemical reactivity upon mixing between an epoxy and an acidic methacrylate resin composition was determined. (As a definition, the gel time here is the interval of time required for the flowable resin composition to become a semisolid jelly or viscosity build-up significantly from the original pasty consistence). The gel time is recorded in Table 2.

TABLE 1

Epoxy and acidic methacrylate paste composition.

| Paste | Resin | Paste composition |
|---|---|---|
| E11 | UVR6110 | 50% resin, 50% GI |
| E12 | BFDGE/TEGDMA (90/10) | 50% resin, 50% GI |
| E13 | BADGE/TEGDMA (90/10) | 50% resin, 50% GI |
| E14 | RDGE | 38% resin, 62% GI |
| E15 | NGDGE | 34% resin, 66% GI |

TABLE 1-continued

Epoxy and acidic methacrylate paste composition.

| Paste | Resin | Paste composition |
|---|---|---|
| M11 | 4-MET/HEMA (67/33) | 50% resin, 50% BiOCl |
| M12 | MMA | 41% resin, 2% R7200, 57% BiOCl |
| M13 | BEPMA | 43% resin, 2% R7200, 55% BiOCl |
| M14 | EGPMA | 43% resin, 2% R7200, 55% BiOCl |

TABLE 2

Epoxy and acidic methacrylate paste curing test.

| Curing test | Gel time at RT | Gel time at 38° C. |
|---|---|---|
| E11-M11 | 3 hrs | 1 hr |
| E11-M12 | 1 hr 30 min | 30 min |
| E11-M13 | 10 sec | <5 sec |
| E11-M14 | 10 sec | <5 sec |
| E12-M11 | >24 hrs | 15 hrs |
| E12-M12 | >24 hrs | >24 hrs |
| E12-M13 | 2 hrs | 30 min |
| E13-M13 | 2 hrs | 30 min |
| E14-M13 | 2 hrs | 30 min |
| E15-M13 | 5 hrs | 1 hr 30 min |

Example 2

Epoxy Resin Cationic Curing Test Monitored by FTIR

Epoxy resin UVR6110 and 4-MET/HEMA/UDMA (in a weight ratio of 60/30/10) resin were mixed in 1:1 weight ratio and maintained at a temperature of 38° C. while the polymerization reaction was monitored by FTIR. After 5 hours at 38° C., it was observed that the composition had an increased viscosity and the epoxy peak in the IR spectrum at 898 cm$^{-1}$ was observed to have decreased intensity relative to when the resins were initially mixed. The disappearance of epoxy peak at 898 cm$^{-1}$, as well as the hardening of mixed resin, were observed after 24 hours of curing at 38° C., indicating the epoxide had undergone a ring-opening polymerization in the presence of 4-MET. It could be visually determined that the cured resin had a dry surface.

Example 3

Epoxy Resin Cationic Curing and Methacrylate Free Radical Curing Test

Light initiator CQ (0.4%) and co-initiator EDMAB (1.0%) were added to a sample of UVR6110 resin. Stabilizer BHT (0.02%) and peroxide BPO (2.5%) were added to a sample of 4-MET/HEMA/UDMA (in a weight ratio of 60/30/10) resin. The two resins were mixed in 1:1 weight ratio and the polymerization was monitored by FTIR. The resin hardened after 30 minutes, but the surface remained wet at that time. The observed faster rate of hardening of the resin mixture, as compared to Example 2, indicates that the methacrylate free radical polymerization occurred before the epoxide ring-opening polymerization. The surface layer demonstrated a curing behavior similar to Example 2, however. A subsequent FTIR scan of the surfaced layer was conducted at 5 hours and 24 hours after the cure and showed a similar disappearance of the epoxy peak at 898 cm$^{-1}$, as in Example 2.

Example 4

Paste-Paste Epoxy Cationic Curing and Methacrylate Free Radical Curing Test

Each resin in Example 2 and Example 3 was mixed with fillers to obtain a flowable consistency. The paste compositions are listed in Table 3. The curing test was performed by mixing 1:1 weight ratio of epoxy paste and methacrylate paste. Gel time was tested at both room temperature and 38° C. The test results were shown in Table 4.

TABLE 3

Epoxy and methacrylate paste composition.

| Paste | Resin | Paste composition |
|---|---|---|
| E41 | UVR6110 in Example 2 | 47% resin, 1% R7200, 15% GI, 25% BiOCl, 12% Ca$_3$(PO$_4$)$_3$ |
| E42 | UVR6110 in Example 3 (contains CQ & EDMAB) | 47% resin, 1% R7200, 15% GI, 25% BiOC, 12% Ca$_3$(PO$_4$)$_3$ |
| M41 | 4-MET/HEMA/UDMA 60/30/10 in Example 2 | 49.5% resin, 0.5% R7200, 50% BiOCl |
| M42 | 4-MET/HEMA/UDMA 60/30/10 in Example 3 | 49.5% resin, 0.5% R7200, 50% BiOCl |

TABLE 4

Epoxy and methacrylate paste curing test.

| Curing test | Gel time at RT | Gel time at 38° C. |
|---|---|---|
| E41-M41 | 24 hr | 12 hr |
| E42-M42 | 2 hr | 40 min |

A significantly faster curing rate was observed for the epoxy/methacrylate composition containing the peroxide free radical polymerization initiator, as shown in Table 4. Moreover, the E42-M42 system is also light curable. The dual cure (light and self-curable) nature and working time is suitable for root canal sealant applications.

Example 5

Property Test of Cured Epoxy/Methacrylate Compositions as Root Canal Sealant

The epoxy paste E42 and acidic methacrylate paste M42 were mixed in 1:1 weight ratio and the properties were tested and summarized in Table 5. The surface residue monomer of the cured paste was evaluated by measuring the removable/wipable surface residue monomer amount. The catalyst and base paste, 0.25 g each, were mixed and the resultant paste was applied as a film to a glass slide without covering the film. The paste was spread on the glass slide in a way that the film thickness of the paste varied from approximately 0.1 mm to 1.0 mm After the paste gelled at room temperature, it was placed under different conditions: 1) room temperature for over 24 hours, 2) 37° C. for over 12 hours without moisture, 3) 37° C. for over 24 hours with 100% humidity. The glass slide, which included the cured sealer material, was first weighed to obtain an original weight, then the surface of the cured sealer material was wiped with lint free Kimwipes®. The glass slide was weighed again to obtain a final weight. The residue monomer % value was calculated as the weight percent difference of the final weight and the original weight.

For physical properties evaluation, the pastes were mixed and set at 37° C. for 24 hours, and then stored at 37° C. in water for 24 hours for the flexural strength (FS) testing and 1 week for water absorption (WA) and water solubility (WS) testing in reference to ISO 4049 (Dentistry—Polymer-based filling, restorative and luting materials) method for the sample dimensions and sizes.

TABLE 5

Summary of cured epoxy/methacrylate compositions as root canal sealant.

| Property tested | Property value |
|---|---|
| Residue monomer % | |
| RT over 24 hrs | 0 |
| 37° C. over 12 hrs no moisture | 0 |
| 37° C. over 12 hrs 100% humidity | 0 |
| FS (MPa) | 51 |
| WA (μg/mm$^3$/week) | 52 |
| WS (μg/mm$^3$/week) | 0 |

Two commercial epoxy resin-based root canal sealers (AH Plus Jet® and AH Plus® Silver free); one commercial acid-containing methacrylate resin based root canal sealant (Epiphany® SE); and one self-etching (SE) root canal sealant (RCS) composition according to an embodiment of the present invention ("Exp. SE RCS") were tested for dimensional change and 24 hours' solubility according to ADA/ANSI Specification No. 57 "Endodontic Sealing Material". A comparison of the results is shown below in Table 6.

TABLE 6

Water solubility and expansion.

| Material | Manufacturer | Lot# | Expansion[1] % | Solubility[2] |
|---|---|---|---|---|
| Exp. SE RCS | Pentron Clinical Tech. | Experimental | 1.00 | 0.003 |
| AH Plus Jet | Dentsply | 0801000301 | 0.64 | 0.01 |
| AH 26 Silver Free | Dentsply | 0710000944 | 3.2 | 0.08 |
| Epiphany SE | Pentron Clinical Technologies | 163647 | 3.5 | 0.13 |

[1]Expansion is the linear percentage change after 30 days in distilled water.
[2]Weight percent soluble in distilled water after 24 hours.

Example 6

Self-Adhering Root Canal Sealant Tooth Bonding Test

Bonding strength of the Exp. SE RCS composition to dentin was compared to a self-etch sealant (Epiphany® SE); an acid-containing methacylate resin-based self-etch root canal sealant (Pentron Corp.); and an epoxy-amine based root canal sealer material (AH Plus® Jet), which is packaged in a double barrel dental syringe like the Epiphany® SE. Six rods (3 mm in diameter, 6 mm height cylinder) were made using each of the materials being tested. Similar to a conventional dentin bonding test, coronal dentin surface was exposed and ground first (n=6). The dentin surfaces were subjected to a standard endodontic cleaning procedure using 5% sodium hypochlorite (NaOCl) and 17% ethylenediamine tetraacid (EDTA) solutions sequentially (Epiphany Instruction of Use, Pentron Corp.). The rods were then applied and adhered onto the dentin surface using the corresponding sealer as the cement there between the rod and dentin surface under a pressure load of a 500 gram weight on top of the composite rod. The excess sealer was removed using a spatula. The sealant was first light cured for 30 seconds from two sides of the composite rod and then removed from load and further self-cured (allow to stand on bench) for 30 minutes before transferring into a container with 100% humidity in a 37° C. oven for 48 hours. Because AH Plus Jet® material is epoxy-amine chemically-cured and the working and setting times are much longer, the bonding samples were allowed to set on bench under the 500 gram load for at least 24 hours before transferring to the 37° C. oven. Bonding strengths were then tested by breaking the composite rod off the dentin surface using an ATS Universal Testing Machine with a push-shear direction. The load was then recorded and the bonding strength was calculated using the load divided by the surface area of the rod adhering to the dentin surface. The test results are shown in Table 7 below. As can be seen, the bonding strength to dentin of the Exp. SE RCS of the invention is unexpectedly much better over the current commercially available Epiphany® SE sealant and the AH Plus Jet® epoxy-based sealer.

TABLE 7

Bonding strength of self-etch/self adhering root canal sealant on dentin surface.

| Sealant | Epiphany SE[2] | Exp. SE RCS | AH Plus Jet[3] |
|---|---|---|---|
| Bonding strength[1] (MPa) | 2.4 (1.0) | 6.3 (2.5) | 0.39 (0.1) |

[1]Bonding strength to Dentin (MPa)
[2]Lot# 162744
[3]Lot# 0801000301

As can be seen from the data in Table 7, the bonding strength of the Exp. SE RCS demonstrates about a 2.5 times increase in bonding strength, as compared to the methacrylate resin based composition with acidic methacrylate monomer (Epiphany® SE), and about a 16 times increase over that of an epoxy resin-based composition using epoxy-amine root canal sealer (AH Plus Jet®). The Exp. SE RCS, as formulated, can therefore be used as a root canal filling material, either alone or in combination with a conventional root canal filling material such as a Gutta Percha cone, a RealSeal point made from Resilon™ material, a carrier based point such as ThermaFil™ (product of Dentsply) or RealSeal 1™ (product of SybronEndo), in a dental root canal treatment procedure.

Example 7

Property Test of Another Experimental Self-Etching Root Canal Sealer (SE RCS)

In this example, Epoxy 06 was used as replacement of UVR6110 because Dow discontinued the chemical supply. Radio-opacifier filler calcium tungstate and barium sulfate were used to replace bismuth oxychloride. The formulation of this experimental self-etch root canal sealer is shown in Tables 7a and 7b.

TABLE 7a

Catalyst paste formulation.

| Catalyst paste composition | Catalyst paste composition (wt %) |
|---|---|
| 4-META | 27 |
| HEMA | 13.5 |
| UDMA | 4.5 |
| BHT | 0.09 |

TABLE 7a-continued

Catalyst paste formulation.

| Catalyst paste composition | Catalyst paste composition (wt %) |
|---|---|
| BPO | 1.11 |
| Silane-treated barium glass filler | 25.8 |
| Barite | 28 |

TABLE 7b

Base paste formulation.

| Base paste composition | Base paste composition (wt %) |
|---|---|
| Epoxy 06 | 28.45 |
| CQ | 0.15 |
| EDMAB | 0.3 |
| DHEPT | 0.05 |
| Y#8087 pigment | 0.05 |
| Silane-treated fumed silica | 2 |
| Barite | 9 |
| Calcium Tungstate | 52 |
| GI | 8 |

Properties were tested on this experimental SE RCS. The residue monomer %, FS, expansion and solubility tests were performed as describe in Example 5. Bonding strength test was performed as described in Example 6. The properties are summarized in Table 8.

TABLE 8

Property summary of experimental SE RCS.

| Property tested | Property value |
|---|---|
| Residue monomer % | |
| RT over 24 hrs | 0 |
| 37° C. over 12 hrs no moisture | 0 |
| 37° C. over 12 hrs 100% humidity | 0 |
| FS (MPa) | 41 (4) |
| Expansion (%) | 2.63 |
| Water Solubility (%) | 0.08 |
| Bonding strength to dentin (MPa) | 6.03 (2.77) |

While the present invention has been illustrated by the description of one or more embodiments thereof, and while the embodiments have been described in considerable detail, they are not intended to restrict or in any way limit the scope of the appended claims to such detail. For example, dental applications have been described for embodiments of the invention, but other non-dental applications may likewise benefit from the inventive composition. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept.

What is claimed is:

1. A two-part polymerizable dental root canal sealer composition comprising:
a first part comprising a cycloaliphatic epoxy compound, a free radical initiator system including a photo-initiator and a tertiary amine polymerization accelerator, and an acid-reactive filler; and
a second part comprising a polymerizable, ethylenically-unsaturated resin having an acid functional group selected from 4-methacryloxyethyl trimellitic anhydride, 4-methacryloxyethyl trimellitic acid, adduct reaction product of pyromellitic di-anhydride with 2-hydroxyethylmethacrylate, adduct reaction product of pyromellitic di-anhydride with glycerol dimethacrylate, or adduct reaction product of benzenetetracarboxylic acid di-anhydride with 2-(6-hydroxy-1-oxo-hexyloxy) ethyl methacrylate, a polymerizable ethylenically-unsaturated resin without an acid functional group, and a self-cure free radical initiator system,
wherein free-radical polymerization of the polymerizable ethylenically-unsaturated resin and epoxy-ring opening polymerization of the cycloaliphatic epoxy compound are initiated upon mixing of the first and second parts to form a dental root canal sealer; and wherein contact between the acid-reactive filler and the acidic functional group upon mixing of the first and the second parts effects an ionic reaction of the acidic functional group and a surface of the acid-reactive filler.

2. The dental root canal sealer composition of claim 1, wherein the self-cure free radical initiator system comprises a peroxide compound.

3. The dental root canal sealer composition of claim 1, wherein the second part further comprises a non-epoxy-containing polymerizable compound having no acid functional group.

4. The dental root canal sealer composition of claim 1, wherein the polymerizable, ethylenically-unsaturated resin having the acid functional group is 4-methacryloxyethyl trimellitic anhydride, 4-methacryloxyethyl trimellitic acid, or a combination thereof.

5. The dental root canal sealer composition of claim 1, wherein the second part further comprises an ethylenically unsaturated phosphoric acid ester having the general formula:

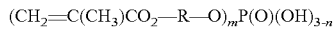

$(CH_2=C(CH_3)CO_2-R-O)_mP(O)(OH)_{3-n}$ wherein R is a substituted or unsubstituted alkyl or aryl group having about 1 to about 36 carbon atoms and n equals 1 or 2.

6. The dental root canal sealer composition of claim 1, wherein the cycloaliphatic epoxy compound includes 3,4-epoxycyclohexylmethyl-3,4-epoxycyclohexane carboxylate, 3,4-epoxy-2-methylcyclohexylmethyl-3,4-epoxy-2-methylcyclohexane carboxylate, or bis(3,4-epoxy-6-methylcyclohexylmethyl)adipate.

7. A kit comprising:
the polymerizable composition of claim 1, wherein the first part and the second part are provided in packaging that physically separates the first part from the second part; and
instructions for mixing to effect a self-cure.

8. The kit of claim 7, wherein the instructions further include a light cure step.

9. The polymerizable dental root canal sealer composition of claim 1, wherein the polymerizable, ethylenically-unsaturated resin having the acid functional group is 4-methacryloxyethyl trimellitic anhydride, 4-methacryloxyethyl trimellitic acid, or a combination thereof; and wherein the cycloaliphatic epoxy compound includes 3,4-epoxycyclohexylmethyl-3,4-epoxycyclohexane carboxylate, 3,4-epoxy-2-methylcyclohexylmethyl-3,4-epoxy-2-methylcyclohexane carboxylate, or bis(3,4-epoxy-6-methylcyclohexylmethyl) adipate.

10. The polymerizable dental root canal sealer composition of claim 1, wherein the cycloaliphatic epoxy compound comprises 3,4-epoxycyclohexylmethyl-3,4-epoxycyclohexane carboxylate, the photo-initiator comprises camphorquinone, the tertiary amine polymerization accelerator comprises ethyl-4-dimethyl benzoate, the polymerizable, ethylenically-unsaturated resin having the acid functional group comprises 4-methacryloxyethyl trimellitic anhydride, and the self-cure free radical initiator system comprises benzoyl peroxide.

11. The polymerizable dental root canal sealer composition of claim 1, wherein a weight ratio between the cycloaliphatic epoxy compound and the polymerizable, ethylenically-unsaturated resin having the acid functional group is in a range from about 1:10 to about 10:1.

12. The polymerizable dental root canal sealer composition of claim 1, wherein the first part is free of polymerizable resins having an acid functional group and epoxy addition reaction polymerization initiators, and wherein the second part is free of epoxy resin.

13. A polymerizable dental root canal sealer composition comprising a first part and a second part that upon mixing has three distinct polymerization mechanisms, the composition comprising:
    a cycloaliphatic epoxy compound in the first part,
    a polymerizable, ethylenically-unsaturated resin having an acid functional group in the second part, the acid functional group selected from 4-methacryloxyethyl trimellitic anhydride, 4-methacryloxyethyl trimellitic acid, adduct reaction product of pyromellitic di-anhydride with 2-hydroxyethylmethacrylate, adduct reaction product of pyromellitic di-anhydride with glycerol dimethacrylate, or adduct reaction product of benzene-tetracarboxylic acid di-anhydride with 2-(6-hydroxy-1-oxo-hexyloxy)ethyl methacrylate,
    a polymerizable ethylenically-unsaturated resin without an acid functional group in the second part, and
    a dual-cure free radical polymerization system including a photo-initiator for light-cure in the first part and a redox system for self-cure, the redox system including a reducing agent in the first part and a peroxide oxidizing agent in the second part, the dual-cure free radical polymerization system including a tertiary amine in the first part as a polymerization accelerator and/or as the reducing agent,
    wherein free-radical polymerization of the polymerizable ethylenically-unsaturated resins in the second part by self-cure using the redox system and epoxy-ring opening polymerization of the cycloaliphatic epoxy compound using the acid functional group are initiated upon mixing of the first and second parts to form a dental root canal sealer; and wherein free-radical polymerization of the polymerizable ethylenically-unsaturated resins in the second part by light-cure using the photo-initiator is initiated upon mixing of the first and second parts with an addition of visible light, and
    wherein the first part is free of polymerizable resins having an acid functional group and epoxy addition reaction polymerization initiators, and wherein the second part is free of epoxy resin.

14. The polymerizable dental root canal sealer composition of claim 13, further comprising an acid-reactive filler in the first part to provide a fourth polymerization mechanism wherein contact between the acid-reactive filler and the acidic functional group upon mixing of the first and the second parts effects an ionic reaction of the acidic functional group and a surface of the acid-reactive filler.

15. The polymerizable dental root canal sealer composition of claim 14, wherein the second part further comprises a non-epoxy-containing polymerizable compound having no acid functional group.

16. The polymerizable dental root canal sealer composition of claim 14, wherein the polymerizable, ethylenically-unsaturated resin having the acid functional group is 4-methacryloxyethyl trimellitic anhydride, 4-methacryloxyethyl trimellitic acid, or a combination thereof.

17. The polymerizable dental root canal sealer composition of claim 14, wherein the second part further comprises an ethylenically unsaturated phosphoric acid ester having the general formula:

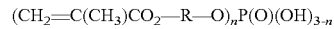

(CH$_2$=C(CH$_3$)CO$_2$—R—O)$_n$P(O)(OH)$_{3-n}$ wherein R is a substituted or unsubstituted alkyl or aryl group having about 1 to about 36 carbon atoms and n equals 1 or 2.

18. The polymerizable dental root canal sealer composition of claim 14, wherein the cycloaliphatic epoxy compound includes 3,4-epoxycyclohexylmethyl-3,4-epoxycyclohexane carboxylate, 3,4-epoxy-2-methylcyclohexylmethyl-3,4-epoxy-2-methylcyclohexane carboxylate, or bis(3,4-epoxy-6-methylcyclohexylmethyl)adipate.

19. The polymerizable dental root canal sealer composition of claim 14, wherein a weight ratio between the cycloaliphatic epoxy compound and the polymerizable, ethylenically-unsaturated resin having the acid functional group is in a range from about 1:10 to about 10:1.

20. A kit comprising:
    the polymerizable composition of claim 13, wherein the first part and the second part are provided in packaging that physically separates the first part from the second part;
    instructions for mixing to effect a self-cure; and
    instructions to effect a light cure.

* * * * *